(12) United States Patent
Chalmers

(10) Patent No.: US 7,621,187 B2
(45) Date of Patent: Nov. 24, 2009

(54) METHOD AND APPARATUS FOR TESTING OF SHEAR STIFFNESS IN BOARD

(75) Inventor: Ian Chalmers, Rotorua (NZ)

(73) Assignee: Korutest Limited, Rotorua (NZ)

(*) Notice: Subject to any disclaimer, the term of this patent is extended or adjusted under 35 U.S.C. 154(b) by 35 days.

(21) Appl. No.: 11/573,803

(22) PCT Filed: Aug. 19, 2005

(86) PCT No.: PCT/NZ2005/000218

§ 371 (c)(1),
(2), (4) Date: Sep. 21, 2007

(87) PCT Pub. No.: WO2006/019322

PCT Pub. Date: Feb. 23, 2006

(65) Prior Publication Data

US 2008/0276720 A1    Nov. 13, 2008

(30) Foreign Application Priority Data

Aug. 19, 2004 (NZ) .................................... 534785

(51) Int. Cl.
*G01N 3/22* (2006.01)
(52) U.S. Cl. .......................................... 73/847; 73/159
(58) Field of Classification Search ........... 73/760–860, 73/159
See application file for complete search history.

(56) References Cited

U.S. PATENT DOCUMENTS

| | | | |
|---|---|---|---|
| 2,843,390 A | 7/1958 | Huyser | |
| 3,834,219 A * | 9/1974 | Brauer | 73/7 |
| 3,955,409 A | 5/1976 | Moser et al. | |
| 4,116,048 A * | 9/1978 | Appleford et al. | 73/83 |
| 4,958,522 A * | 9/1990 | McKinlay | 73/847 |
| 5,209,124 A * | 5/1993 | Graudejus et al. | 73/821 |
| 5,766,137 A * | 6/1998 | Omata | 600/587 |
| 5,804,707 A * | 9/1998 | Scarton et al. | 73/82 |
| 5,892,157 A | 4/1999 | Syre | |
| 6,050,149 A * | 4/2000 | Yoshizawa | 73/849 |
| 7,354,617 B2 * | 4/2008 | Kamiya et al. | 427/8 |
| 2003/0136199 A1 | 7/2003 | Singleton et al. | |

FOREIGN PATENT DOCUMENTS

| | | |
|---|---|---|
| EP | 0328272 | 8/1989 |
| GB | 1479785 | 7/1977 |
| GB | 2336915 | 11/1999 |
| WO | WO 01/53828 | 7/2001 |

* cited by examiner

*Primary Examiner*—Max Noori
(74) *Attorney, Agent, or Firm*—Dann, Dorfman, Herrell and Skillman, P.C.

(57) ABSTRACT

A method and apparatus for testing shear stiffness in board is disclosed. The board sample (6) is placed into stationary jaw (2) and jaw (3) which is rigidly connected to inertial mass (7). The mass (7) is twisted around the sample axis with an initial twist chosen to ensure the sample is within the elastic region, and then allowed to freely oscillate. The oscillation frequency is then measured to evaluate the torsional stiffness of the sample.

14 Claims, 7 Drawing Sheets

METHOD AND APPARATUS FOR TESTING OF SHEAR STIFFNESS IN BOARD

FIELD OF THE INVENTION

The present invention relates to a method and apparatus for evaluating the shear stiffness of corrugated board.

BACKGROUND

Corrugated board is a paper sandwich construction made by combining three or more paperboard sheets. In its most common form, two paperboard facings are adhered to each side of an inner paperboard sheet which has been formed into a sinusoidal shape. This construction achieves high stiffness and strength with low weight and cost.

Shear stiffness is an important property for corrugated board. If a corrugated board is well specified with strong liners and medium, it will perform as designed, but if the medium is damaged during or after manufacture its strength may be sub-standard.

Flat crush of corrugated board is often used to measure the "strength" of the corrugated board. The flat crush test is performed on a circular sample of a standard area. The specifications for this test are given in Australian Standard 1301.429s-89. A disadvantage of this test method is that it will not discriminate between good undamaged board and corrugated board damaged during processing that feels soft to the touch. This is because the highest crush result occurs after the flutes have been well squashed. Damage to the core material by excessive lateral pressure can severely weaken the core structure. A crushed core exhibits a drastic loss of machine direction global shear stiffness of the core and will also lack hardness and bending stiffness.

Shear stiffness is a fundamental structural property of a sandwich panel and is defined by:

$$\text{Shear\_Stiffness} = \frac{\text{Shear\_Force}}{\text{Shear\_Strain}} \qquad \text{Eq. 1}$$

Shear stiffness in the machine direction is designated as $G_{xz}$ and in the cross direction global as $G_{yz}$.

U.S. Pat. No. 3,955,409 discloses a device for torsional oscillation testing of plastics materials.

U.S. Pat. No. 4,958,522 describes a method for determining the shear stiffness of corrugated board by mounting and twisting a test piece between two clamps. Measurements are taken of the angle of twist and the force applied using a rotary encoder and a load cell. In use of this technique for quality assessment of corrugated board it is assumed that with all else being equal (liner compression etc) damage during conversion is the main cause of poor corrugated board performance and the shear test will show up this damage.

SUMMARY OF THE INVENTION

In a first aspect, the present invention broadly consists in a method for testing the torsional stiffness of a sample of board, including:

holding a sample of corrugated paper board at one part and attaching an inertial mass to another part of the sample;
initially rotating the inertial mass about an axis of the sample and then;
allowing the inertial mass to freely oscillate;
measuring the time period for one or more oscillation(s) of the sample; and obtaining an indication of the stiffness of the sample by reference to the time period of said one or more oscillations.

Preferably said indication of the stiffness of the sample is the angular frequency of the oscillation(s) or a value derived from the angular frequency of the oscillation(s).

Preferably the method includes assessing the torsional modulus of the sample by reference to the angular frequency of the oscillations, the polar moment of inertia of the inertial mass and the cross-sectional area and length of the sample.

In a second aspect, the present invention broadly consists in an apparatus for testing the torsional stiffness of a sample of corrugated board including:

means for holding the samples so that one part of the sample carrying an inertial mass may be rotated relative to another part of the sample about an axis of the sample and then allowed to oscillate;
a detector for detecting when the inertial mass passes through a zero angle region when the sample oscillates; and
electronic processing means arranged to obtain an indication of the shear stiffness of the sample by reference to the time period of one or more oscillations of the sample.

Preferably, the apparatus may further include means for measuring the angular displacement of the inertial mass relative to the axis of the sample.

Preferably, the indication of the stiffness of the sample is the angular frequency of the oscillation(s) or a value derived from the angular frequency of the oscillation(s).

Preferably, the detector comprises an optical pickup fixed to the frame and a finger fixed to the inertial mass for detecting when the inertial mass passes through the zero angle region when the sample oscillates.

The term 'comprising' as used in this specification and claims means 'consisting at least in part of', that is to say when interpreting independent claims including that term, the features prefaced by that term in each claim all need to be present but other features can also be present.

BRIEF DESCRIPTION OF THE DRAWINGS

The present invention will now be described with reference to the accompanying drawings in which.

DETAILED DESCRIPTION

Figure 1:
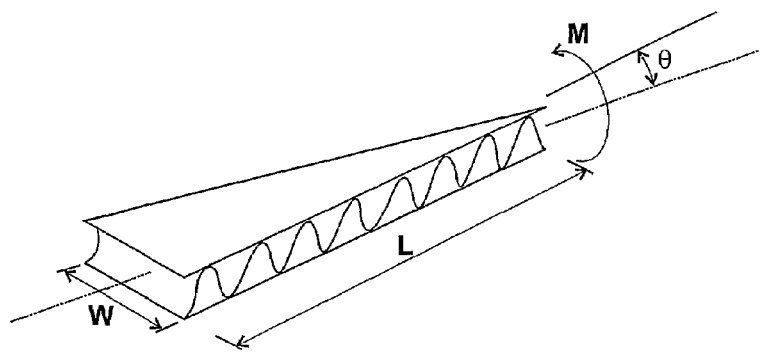
FIG. 1 shows a strip of corrugated board subjected to a twisting moment.

FIG. 1 shows a strip of corrugated board subjected to a twisting moment, M, which is symmetric about the axis of the board. A shear field is developed in the fluting such that no shear exists along the centre of the sample and the amount of shear on either side of the centre is equal and opposite.

Shear stiffness is a fundamental structural property of a sandwich panel and as mentioned before, is defined by:

$$\text{shear stiffness} = \frac{\text{shear force}}{\text{shear strain}}$$

The twisting stiffness of the sample can therefore be defined as $$D_{QM} = \frac{M}{\theta} \frac{L}{w} \qquad \text{Eq 3}$$

where, $D_{QM}$=machine direction (MD) twisting stiffness (Nm)
M=twisting moment (Nm)
θ=angle of twist (radians)
L=sample length between clamps (m)
w=width of sample (m)

The total twisting stiffness is a combination of the twisting stiffness of the liners and the fluting. However, if the angle of twist is kept sufficiently small and the thickness of the liners is thin relative to the fluting height, the shear strains of the liners themselves can be considered to be negligible. Hence, it is possible to introduce a relatively large shear force in the fluting, but without large shear strains occurring in the facings. Finite element analysis reported by McKinlay (Amcor), at the 10$^{th}$ Fundamental Research Symposium, Oxford September 1993, has been used to show that a fundamental relationship exists between the MD shear stiffness of corrugated board (CB) and the MD twisting stiffness, as measured above, according to (Eq 4):

$$\frac{D_Q}{D_{QM}} = 3 + \{1 + a + b\} \frac{3D_Q}{5tG_{12}} \left\{ \frac{w}{h} \right\}^2 \qquad \text{Eq 4}$$

Where $D_Q$=MD shear stiffness
$D_{QM}$=MD twisting stiffness
a=0.028
b=0.018
t=thickness of liner
$G_{12}$=in-plane shear modulus of liners
w=width of sample
h=flute height Hence, the pure MD shear stiffness of corrugated board can be calculated from simple MD shear twist measurements.

Figure 4:
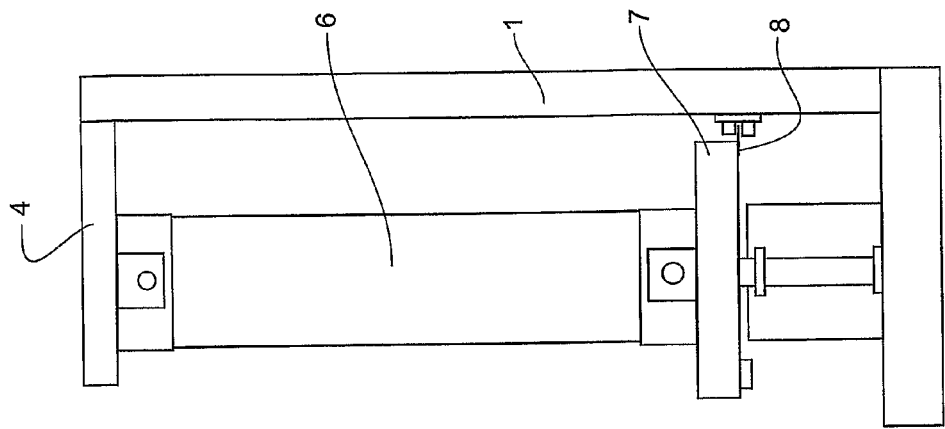
FIG. 4 shows a side view of a first prototype testing apparatus.
Figure 3:
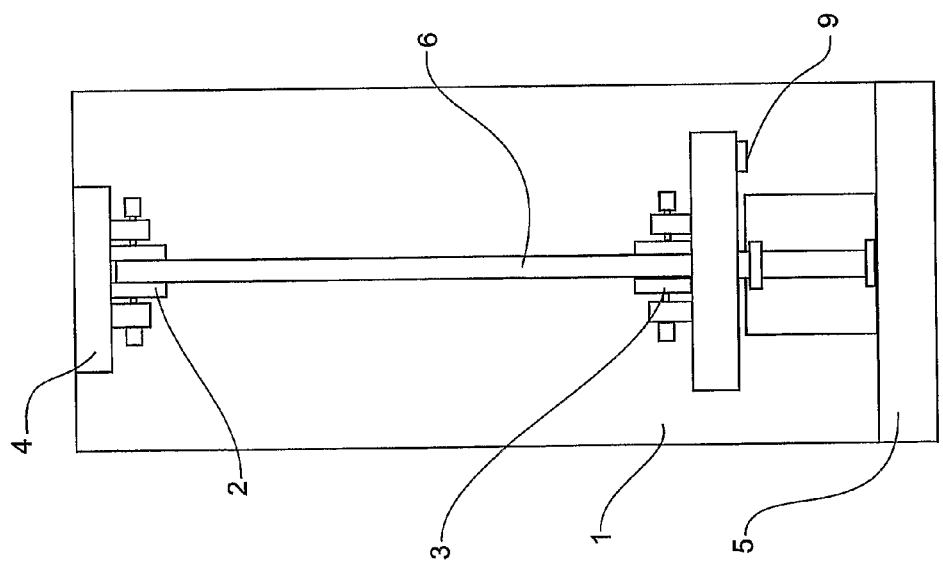
FIG. 3 shows a front view of a first prototype apparatus.

FIGS. 3 and 4 show a first prototype of the corrugated board shear stiffness test apparatus or tester. The tester includes a generally upright frame supported on a base 1, with a first clamp 2 fixed at an upper end of the frame at 4 and a second clamp 3 which is free to rotate at a second end of the base 5. There is a small roller bearing 9 underneath the inertial plate that acts as a point for the mechanical oscillation initiator to contact to start the pendulum rotating. The first and second clamps are axially aligned. An inertial plate 7 is attached to the second clamp. An optical electronic pickup 8 such as a Schmidt trigger optical through scan is also carried by the frame and a narrow finger is fixed to the inertial mass to detect when the torsion pendulum passes through the zero angle region. Alternatively, an optical or electrical device may be fitted to obtain full data on the angular position of the inertial plate.

In use a corrugated board sample 6 is cut square along the machine direction of the corrugator (and paper machine) with parallel edges and no compression applied to the board during the cutting operation. Depending on the size of the tester and the inertial mass, the sample size may for example be of any width from 20 to 100 mm with a span length from 3 to 8 times the width. Preferably, the width is about 25 mm with a free span of about 100 mm.

Figure 6:
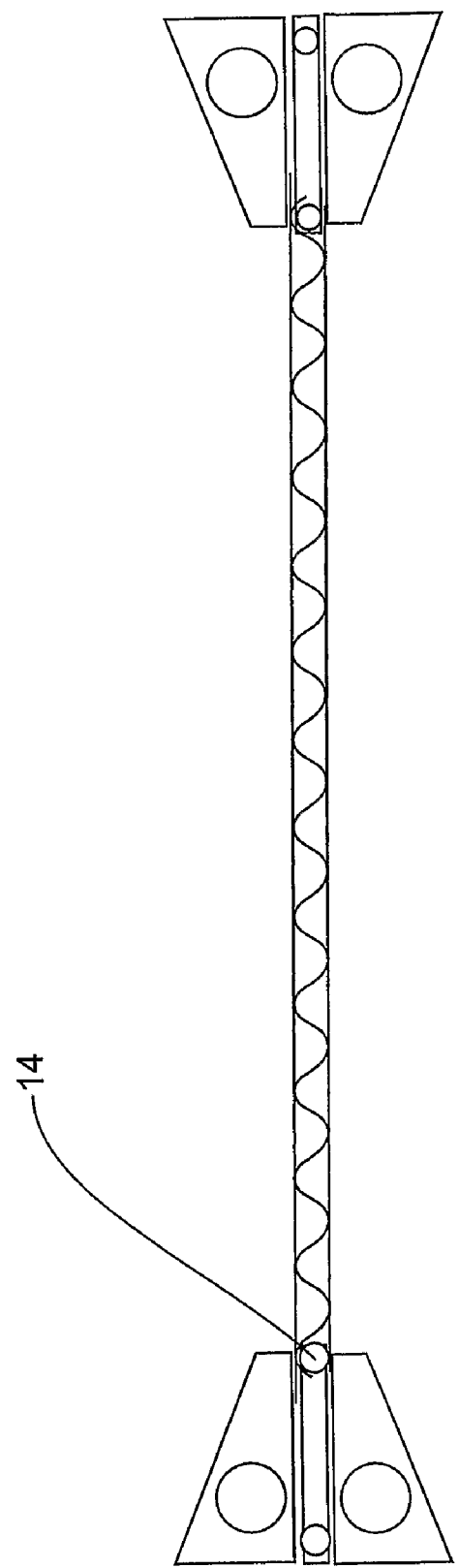
FIG. 6 shows a sample fixed in the second prototype testing apparatus.

The sample 6 is firmly clamped in the jaws 2, 3 of the tester so that the sample is rigidly fixed and cannot move at one end and effectively part of the inertial mass 7 at the other end. The clamp can be engaged using screws, levers, pistons or springs. To effectively hold a sample that is only 10 mm longer than the free span, a post 14 is required that the sample is able to slide over and be clamped against as shown in FIG. 6.

The inertial plate 7 is twisted around the sample axis. The initial angle of twist is chosen to ensure that the shear is within the elastic region. Then the inertial mass is allowed to freely oscillate. Detection of the oscillations by the narrow finger passing through the pickup 8 produces a pulsed output as in FIG. 6. The decay in angular velocity may be measured from the length of the optical pulse produced.

To measure the resonance frequency of a torsional oscillation all that is required is a way to count the pulses on a time base system. Typically the time for the first two cycles is determined in milliseconds and a microcontroller used to calculate the square of the average angular frequency ($\omega^2$) which is output to the LCD.

Figure 2:
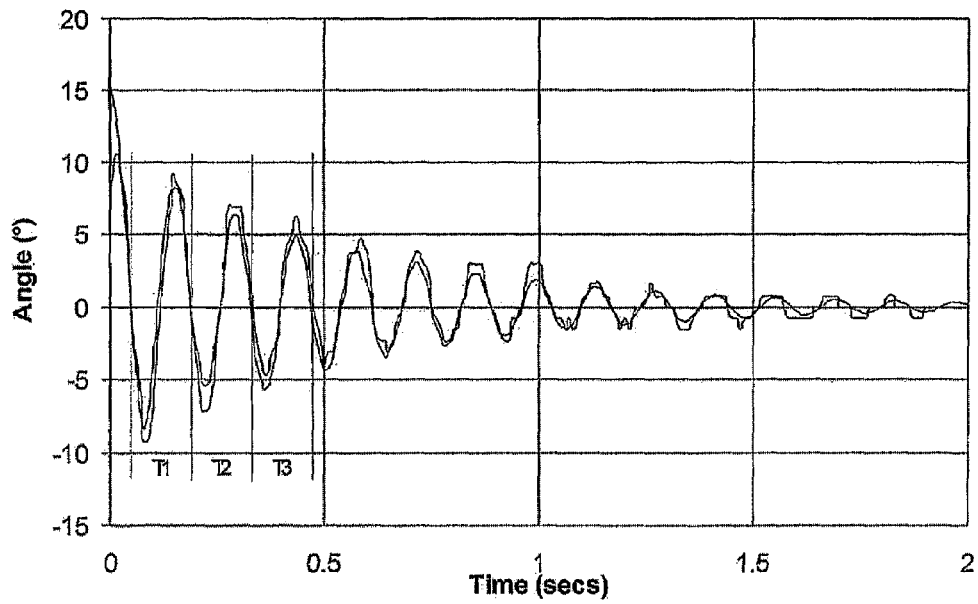
FIG. 2 shows a typical damping curve from a first prototype apparatus with a model equation put through the data.

From the curve in FIG. 2, the frequency ω is measured, and along with the polar moment of inertia and sample dimensions, the shear modulus $G_{zx}$ or $G_{zy}$ can be obtained. If an optical or electrical device is fitted to obtain full data on the angular position of the inertial plate, a curve as in FIG. 2 may also be produced.

The time for an oscillation cycle is easily converted to angular frequency squared ($\omega^2$) which is directly proportional to torsional stiffness. For a quality control application in general the $\omega^2$ is all that is required. Further in-depth scientific information can be obtained by using sample size and moment of inertia calculations.

The tester has a display screen 15 for showing test results or outputs. Typically, the output is the angular frequency squared which has been divided by 100. This brings the range of results for corrugated board down from for example 150-8000 to 1.5-80. These lower numbers are easier to understand and have been termed the "Board Performance Indicator" or BPI. Alternatively, other outputs may be calculated and displayed. For example, shear stiffness, angular frequency, or angular frequency squared.

Because the test is designed to be comparative rather than absolute, the pure stiffness is not required. As a quality control device, the angular frequency squared or BPI are more useful than the pure shear stiffness of the board.

Within one flute type the results are comparable and the influence of different variables are easily identified. For example, different "C" flute profiles, day to day variation of the corrugator, or a change in component weights. Further down the converting operation, the damaging effects of printing pressure are also easily identified. Typical BPI results for some grades are shown in Table 1.

TABLE 1

Typical BPI Results

| Flute | Liner 1 g/m² | Medium Type | Medium g/m² | Liner 1 g/m² | BPI |
|---|---|---|---|---|---|
| B | 145 | RF | 120 | 115 | 9.8 |
| B | 145 | SC | 150 | 175 | 11.8 |
| C | 145 | RF | 120 | 115 | 6.0 |
| C | 175 | RF | 150 | 205 | 10.1 |
| C | 204 | SC | 190 | 205 | 17.5 |
| C | 205 | Laminated SC | 120/120 | 205 | 30.1 |

TABLE 2

Effect Of Crushing On DST Results in a 4.0 mm C Flute Board.

| Crush Depth (mm) | Crush (%) | DST after 1 hour (BPI) | Loss of BPI (%) |
|---|---|---|---|
| 0 | 0 | 22.5 | 0 |
| 0.15 | 3.75 | 20.5 | −8.9 |
| 0.40 | 10.0 | 15.3 | −32.0 |
| 0.65 | 16.25 | 11.0 | −51.1 |

From Table 2, every 1% crush is followed by approximately a 3% loss in DST.

The test is non-destructive in that the same sample can be repeatedly tested if required. The device is simple and quick to use and results are obtained in seconds.

Figure 5:
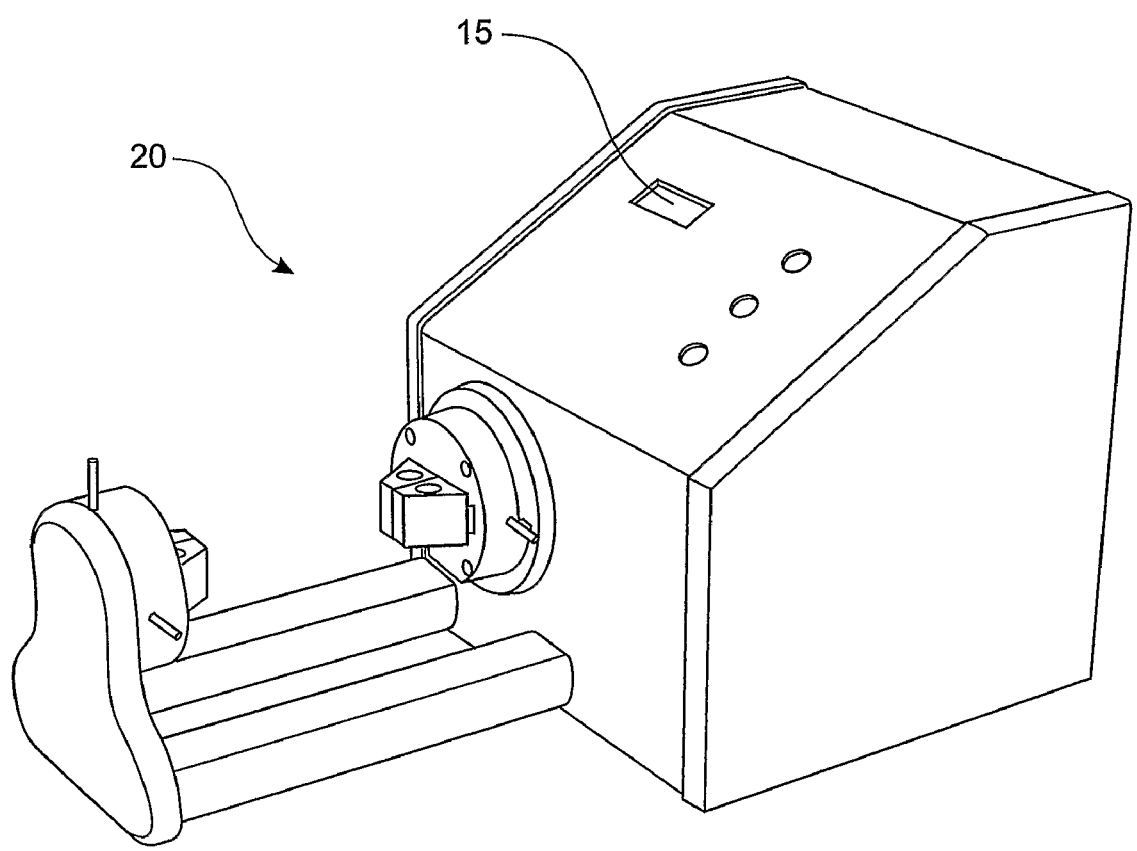
FIG. 5 shows a perspective view of a second prototype testing apparatus.

An alternative corrugated board shear stiffness test apparatus or tester 20 is shown in FIG. 5. The second tester differs from the first tester shown in FIGS. 3 and 4 in that the tester has a horizontal rather than vertical orientation.

The second prototype tester can have any orientation from horizontal to vertical as long as the clamps are perfectly aligned relative to each other. This ensures that the sample is parallel and no compressive forces are applied to the sample. For ease of operation, the preferred sample orientation is horizontal with the sample width at right angles to the x-y plane.

FIG. 5 shows the second prototype tester without a sample in place. With this tester, the clamping pressure is applied via spring tension. Alternatively, the clamping pressure may be applied via screws, levers and/or pistons.

Figure 7:
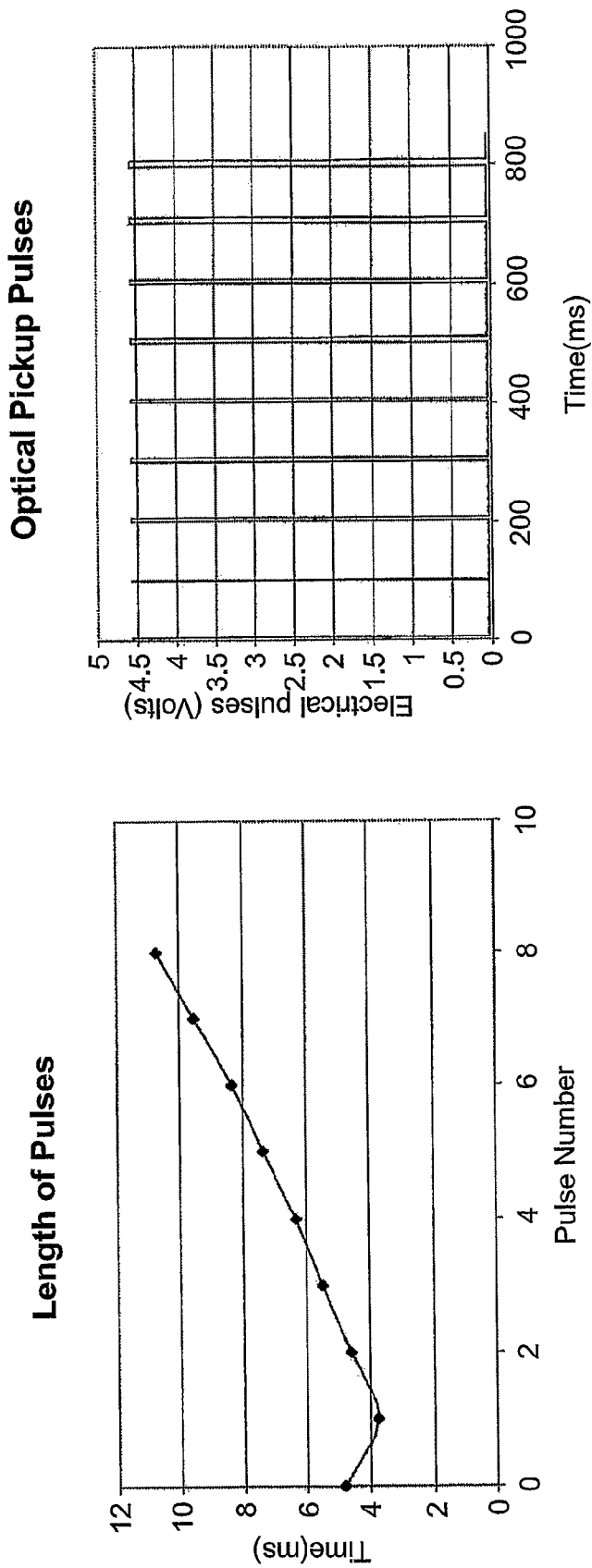
FIG. 7 shows the electrical pulses produced in use of the first prototype testing apparatus.

During studies using a first prototype test apparatus as described, the pickup 8 was monitored by the pico ADC-212 data logger. It was found that after the initial cycle the second cycle sped up then the remaining cycles slowed down as the amplitude reduced. FIG. 7 shows a typical result for a 250/160/250 "C" flute Kraft liner, SC medium corrugated board 36 mm wide with a span of 200 mm. In FIG. 7, the front edge of the first pulse starts the data logger and each pulse occurs at the half cycle where the optical pickup is disturbed by a narrow finger carried by the inertial mass 7 that interrupts the light beam of an optical Schmidt trigger through scan device. The electronics of the testing apparatus may be basic with hard wired logic to sense pulses and time or alternatively, may include microcontroller electronics and calculated output or interfaced to a computer for full data analysis and networked results.

It may be necessary to investigate the stiffness of the sample in various environmental conditions, for example to determine the effect of moisture content. The testing apparatus may be cabled so that the frame and clamp assembly may be used in an environmental cabinet (hand through door) with the electronics external to the cabinet. The electronics may also be sealed hermetically to allow use in an environmental chamber (walk-in) or cool store. Cool store conditions of 95% RH and 1° C. can therefore be used for severe but realistic test conditions.

A body will oscillate in rotational motion if there is a restoring torque that is proportional to the angular displacement of the body from its equilibrium position ie:

$$\tau = -k\theta$$

where $-k$ is the torsion constant of the rod

Combining this with Newton's second law in rotational motion form $$\tau = I\alpha$$

to give $-k_t\theta = I\alpha$ \hfill Eq 7 where I is the moment of inertia of the rotating object and $$\alpha = \frac{d^2\theta}{dt^2}$$

is the angular acceleration of the system. The equation of motion is $$-k_t\theta = I\frac{d^2\theta}{dt^2} \qquad \text{Eq 8}$$

The general solution to this equation is $$\theta = \theta_m \sin(\omega t + \phi) \qquad \text{Eq 9}$$

where $\theta_m$ is the amplitude of the oscillation and
  $\omega$ is the angular frequency where $$\omega = 2\pi f = \frac{2\pi}{T} \text{ radians/sec}$$

where f and T are the frequency and period of the oscillation and $\phi$ is the phase angle.

Of particular note, $\omega$ should not be confused with the rate of change of the displacement $\Delta\theta/\Delta t$, the angular velocity, which normally has the same symbol (omega).

In order that Eq 8 is a solution of Eq 9, the following must apply $$\omega = \sqrt{\frac{k_t}{I}} \qquad \text{Eq 10}$$

or $$k_t = \omega^2 . I$$

The torsion constant $k_t$ depends on the shape of the rod as well as the material. The relation for a solid rod of circular cross section is:

$$k_t = \frac{nA^2}{2\pi L} \qquad \text{Eq 11}$$

or $$n = \frac{k_t 2\pi L}{A^2}$$

where n is the torsion modulus, A is the cross-sectional area of the rod and L is the length of the rod.

For the purposes of an in-plant quality control measure a standard method using one width and the conversion of the time period for one cycle to the square of the angular frequency is more than adequate to determine if the corrugated board has been damaged during manufacture. However, it will be appreciated that in other embodiments the full torsion modulus, torsion constant, torsional stiffness or shear stiffness can be calculated if required. This information is obtained by reference to the angular frequency of the oscillation(s), the polar moment of inertia of the inertial mass, and the cross-sectional area and length of the sample.

Three main samples of corrugated board were tested on the first prototype stiffness tester.

Samples of a standard virgin component "C" flute corrugated board, an RF twin cushion, and an RF "B" flute were tested with a range of sample widths. A very good correlation between shear stiffness as measured using the slope of the stress/strain data (twisting moment) and dynamic stiffness using oscillation pulse data was obtained. The results are shown in FIG. 8.

The Empirical equation relating dynamic frequency of this inertial system to the slope of the MD twisting stiffness is:

MD Twisting Stiffness=$3.329 \times 10^{-4}$*Dynamic Angular Frequency squared ($\omega^2$), $r^2$=0.9974

Figure 8:
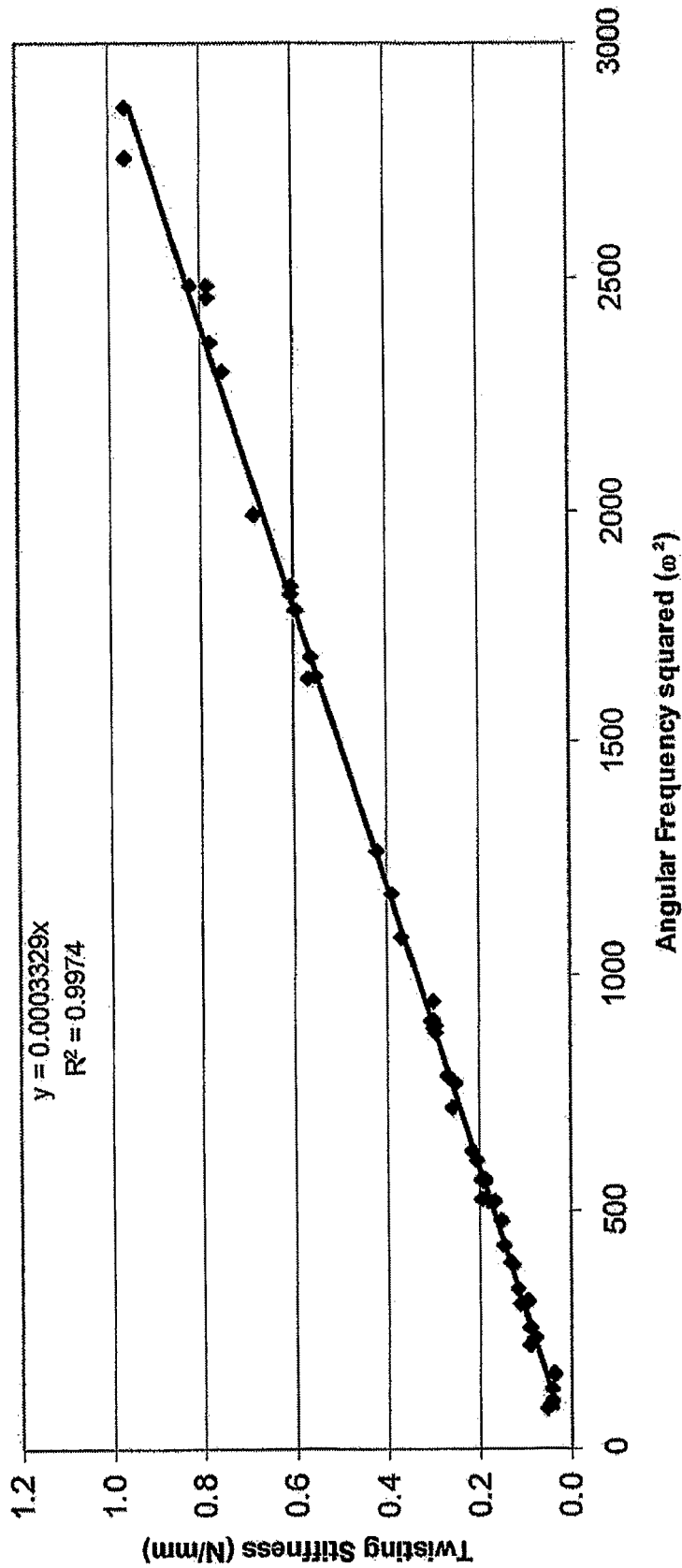
FIG. 8 plots twisting stiffness stress-strain slope versus angular frequency squared, results obtained from testing three different samples of corrugated boards, of different widths.

From FIG. 8 it can be seen that a simple empirical conversion of angular frequency to twisting stiffness can be made and then the shear stiffness calculations using Eq 3 carried on from there to obtain comparative figures to existing data that may be available.

The full torsion modulus can be calculated if required as per the preceding section but angular frequency squared ($\omega^2$) alone would be suitable for an in-house quality control arbiter.

Figure 9:
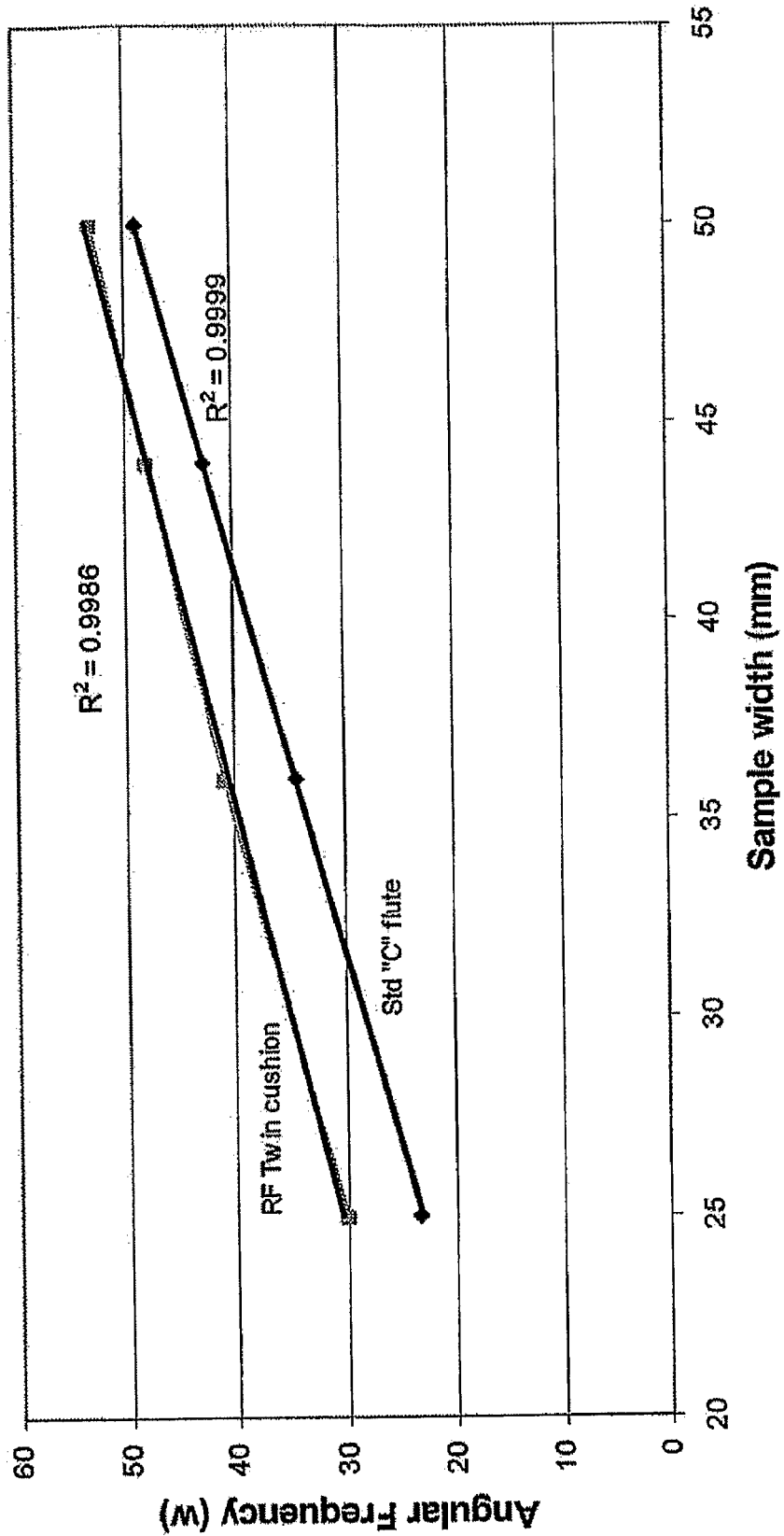
FIG. 9 plots angular frequency versus test piece width for two good quality board samples.

The "B" flute RF corrugated board that was used in the example above had been printed and fully converted with quite a bit of damage on different parts of the box. This variation was picked up by the dynamic stiffness tester with the $\omega^2$ varying from 251 to 408 on different parts of the box. Because of the variability, this sample was not suitable to be used for the exercise that resulted in FIG. 9. FIG. 9 shows how the angular frequency ($\omega$) varies with sample width. The correlation is very good without any sign of an edge effect.

I claim:

1. A method for testing the torsional stiffness of corrugated paper board, including:
    holding a sample of corrugated paper board at one part and attaching an inertial mass to another part of the sample;
    initially rotating the inertial mass about an axis of the sample and then;
    allowing the inertial mass to freely oscillate;
    measuring the time period for one or more oscillation(s) of the sample by detecting the inertial mass passing through a zero angle region as the sample oscillates; and
    obtaining an indication of the stiffness of the sample by reference to the time period of said one or more oscillations.

2. A method as claimed in claim 1 wherein said indication of the stiffness of the sample is the angular frequency of the oscillation(s) or a value derived from the angular frequency of the oscillation(s).

3. A method as claimed in claim 2, further including assessing the torsional modulus of the sample by reference to the angular frequency of the oscillation(s), the polar moment of inertia of the inertial mass, and the cross-sectional area and length of the sample.

4. A method as claimed in claim 3 including assessing the stiffness of the sample by reference to one or two oscillations of the sample.

5. A method as claimed in claim 4 wherein the corrugated paper board comprises two paper board facing layers on either side of a fluted centre layer.

6. An apparatus for testing the torsional stiffness of a sample of corrugated board including:
    means for holding the sample so that one part of the sample carrying an inertial mass may be rotated relative to another part of the sample about an axis of the sample and then allowed to oscillate;
    a detector for detecting when the inertial mass passes through a zero angle region when the sample oscillates; and
    electronic processing means arranged to obtain an indication of the shear stiffness of the sample by reference to the time period of one or more oscillations of the sample.

7. The apparatus as claimed in claim 6, further including means for measuring the angular displacement of the inertial mass relative to the axis of the sample.

8. The apparatus as claimed in claim 7 wherein said indication of the stiffness of the sample is the angular frequency of the oscillation(s) or a value derived from the angular frequency of the oscillation(s).

9. The apparatus as claimed in claim 8 wherein said detector comprises an optical pickup fixed to the frame and a finger fixed to the inertial mass for detecting when the inertial mass passes through the zero angle region when the sample oscillates.

10. The apparatus as claimed in claim 9 wherein said electronic processing means is arranged to obtain said indication of the stiffness of the sample by reference to one or two oscillations of the sample.

11. The apparatus as claimed in claim 10 including clamp means for holding the sample and for attaching the inertial mass to the sample.

12. The apparatus as claimed in any one of claims 6 to 11 also including a display for displaying an output representative of the torsional stiffness of the sample.

13. A method for testing the torsional stiffness of corrugated paper board, including:
    holding a sample of corrugated paper board at one part and attaching an inertial mass to another part of the sample;
    initially rotating the inertial mass about an axis of the sample and then;
    allowing the inertial mass to freely oscillate;
    measuring the time period for one or two oscillation(s) of the sample by detecting the inertial mass passing through a zero angle region as the sample oscillates; and
    obtaining an indication of the stiffness of the sample by reference to the time period of said one or two oscillations.

14. An apparatus for testing the torsional stiffness of a sample of corrugated board including:
    means for holding the sample so that one part of the sample carrying an inertial mass may be rotated relative to another part of the sample about an axis of the sample and then allowed to oscillate;
    a detector comprising an optical pickup fixed to the frame and a finger fixed to the inertial mass for detecting when the inertial mass passes through a zero angle region when the sample oscillates; and
    electronic processing means arranged to obtain an indication of the shear stiffness of the sample by reference to the time period of one or more oscillations of the sample.

* * * * *